United States Patent [19]

Colegrove et al.

[11] Patent Number: 4,874,423

[45] Date of Patent: Oct. 17, 1989

[54] SOLID, HERBICIDAL COMPLEXES

[75] Inventors: George T. Colegrove, San Diego; Thomas A. Lindroth, Spring Valley, both of Calif.

[73] Assignee: Merck & Co., Inc., Rahway, N.J.

[21] Appl. No.: 904,322

[22] Filed: Sep. 8, 1986

Related U.S. Application Data

[63] Continuation-in-part of Ser. No. 785,624, Oct. 8, 1985.

[51] Int. Cl.$^4$ ............................................. A01N 43/36
[52] U.S. Cl. ......................................... 71/95; 71/65; 514/780
[58] Field of Search ................ 435/104; 514/937, 946, 514/947, 970, 780; 424/485, 488, 496; 71/65, 95

[56] References Cited

FOREIGN PATENT DOCUMENTS 174101 8/1985 European Pat. Off. .
84JP-199402 4/1986 Japan .
2181350 10/1985 United Kingdom .

Primary Examiner—Barry S. Richman
Assistant Examiner—T. J. Wallen
Attorney, Agent, or Firm—Gabriel Lopez; Hesna J. Pfeiffer

[57] ABSTRACT

Low viscosity heteropolysaccharides, e.g., xanthan gum, S-194, and guar gum, are disclosed. These gums are especially useful in preparing herbicidal compositions.

4 Claims, No Drawings

SOLID, HERBICIDAL COMPLEXES

CROSS REFERENCE

This is a continuation-in-part of U.S. Ser. No. 785,624, filed Oct. 8, 1985, pending.

BACKGROUND OF THE INVENTION

The use of heteropolysaccharides as viscosifying agents in many food and industrial applications is well known. Typically, these agents are used because of their ability to thicken aqueous solutions at relatively low concentrations. Xanthan gum (a biopolymer produced by aerobic fermentation in a nutrient medium of the organism *X. campestris*), S-194 (a biopolymer produced by aerobic fermentations in a nutrient medium of the Alcaligenes organism ATCC 31961, described in U.S. Pat. No. 4,401,760), and guar gum (an extract of the seed of the guar plant, *Cyanaposis tetragonolobus,* family Leguminosae) are three such known polysaccharides. These gums are known in various forms. For example, guar gum derivatives include oxidized guar, carboxymethylated guar, hydroxyalkylated guar, etc. Xanthan gums of different pyruvate levels (EP 66,961) and calcium levels (e.g., U.S. Pat. No. 4,375,512, Richmon) are known. Xanthan gums of altered rheology have also been described. For example, U.S. Pat. No. 4,299,825 teaches a "low viscosity" xanthan gum having an 8-15 wt. % viscosity of 10,000-20,000 cP.

Bipyridinium (also known as bipyridylium) quaternary salts such as those of U.S. Pat. No. 4,118,218 are useful herbicidal compounds. Of these, paraquat (1,1'-dimethyl-4,4'-bipyridinium dichloride) and diquat (6,7-dihydrodipyrido (1.2-a; 2'.1'-c) pyrazinediium dibromide) are the most commonly used. These compounds are typically sold commercially as aqueous compositions. Attempts at preparing free flowing wettable powder formulations of these salts have not proved successful. UK 2,100,603 describes wettable powder compositions using powdered calcium silicate as a carrier. J5 6152-401 (Asahi Chemical) describes powdered compositions comprising inorganic sulphate salts of sodium, magnesium, etc. and anti-caking compounds such as white carbon, borax, silica gel, etc. U.S. Pat. No. 4,118,218, which is incorporated herein by reference, describes a process for preparing granular herbicidal compositions which comprises depositing an aqueous solution of the bipyridinium quaternary salts on inert carriers, preferably calcium or sodium chloride. This patent also refers to various Japanese and U.K. patent applications which teach solid herbicidal compositions. None of these compositions has been commercially successful. Generally, the prior art compounds have not been sufficiently concentrated in active ingredients, have not hydrated properly, or have not prevented crystallization of the active ingredient, thus posing a potential hazard to handlers of the dry powders. Crystallization occurs on drying of aqueous solutions of the herbicidal bipyridinium salts. Crystals also appear in the dry compositions of these salts.

SUMMARY OF THE INVENTION

Very low viscosity heteropolysaccharides have now been prepared. They are useful in preparing highly concentrated solid bipyridinium salt herbicidal compositions. The compositions exhibit no surface crystallization. Additionally, these low viscosity heteropolysaccharides are useful in other industrial and agricultural applications.

DETAILED DESCRIPTION

The low viscosity polysaccharides of this invention are low viscosity xanthan gum, low viscosity S-194, and low viscosity guar. By low viscosity xanthan gum or S-194 is meant a gum having a viscosity of 15-300 cP (5% (wt.) solution as measured on a Brookfield LVT Viscometer at 25° C., 60 rpm, spindle no. 2). Preferably, the viscosity is 200-300 cP. By low viscosity guar is meant a guar gum having a viscosity of 15-100 cP, at 5% (wt.) solution, measured as above. Preferably, the viscosity is 50-100 cP.

The low viscosity polysaccharides can be prepared by various means. One process uses hydrogen peroxide in a formulation similar to Fenton's Reagent. The formulation contains 0.15-0.25% $H_2O_2$, 0.05% $FeSO_4$ and 0.10% EDTA ethylenedinitrilo tetraacetic acid tetrasodium salt. Using this formulation a 10% clarified guar paste can be degraded from a viscosity of greater than 10,000 cP, spindle 4 at 60 rpm, to about 150 cP in 15 minutes at 60° C. A 4% xanthan gum solution can be degraded from 5000 cP to 20 cP in 30 minutes at 60° C. Degradation rate is proportional to peroxide concentration and temperature. The amount of peroxide required increases with gum impurity.

Guar can also be degraded using enzymes. For example, 0.1% hemicellulase at pH 5.0 degrades a 10% guar dispersion from greater than 10,000 cP to 280 cP at 50° C. in 48 hours. An alternative enzyme is galactomannase. Hemicellulases and galactomannases are commercially available.

Following degradation the low viscosity polysaccharides are recovered from solution by precipitation with 2-3 volumes of isopropanol, followed by drying and milling.

The low viscosity polysaccharides of this invention are useful in a variety of industrial and agricultural applications. Such uses include textile printing and dyeing, especially in foamed dye or ink formulations, especially as anti-migrant agents; paper printing, especially foamed ink formulations; petroleum operations, including oil well drilling muds; lithography, as in lithographic fountain solutions, especially as gum arabic replacers; detergents; microencapsulation; inks, especially as stabilizers for water-based inks; ceramics; protective colloids; agricultural foam markers; fire fighting foams, including fluoro- and non-fluoro-based proteins and non-protein agents; coatings, especially as suspending agents for high-solids paper coatings; emulsions, as stabilizers; latex adhesives, as viscosifiers; binders for the agglomeration of powders; binders for water soluble pesticides; mortars and cements, as moisture control agents; wall materials in complex coacervation microencapsulation; and dispersants for raw mineral slurries.

In some applications, as when the degraded polysaccharides are to be complexed to form the herbicidal compositions of this invention, initial recovery of the degraded gum can be eliminated and further processing such as complex-formation can be performed in situ. Thus, another aspect of this invention is an aqueous solution comprising low viscosity heteropolysaccharides. More specifically, broken fermentation broth is a useful aqueous solution of xanthan gum or S-194.

The compositions of this invention include solid, herbicidal bipyridinium quaternary salt/polysaccharide complexes comprising 14-55% (wt.) bipyridinium salt, calculated as cation. The polysaccharide is canthan, S-194, or guar or a blend thereof of low viscosity. The bipyridinium salt is preferably one of:

1,1'-ethylene-2,2'-bipyridylium dibromide,
1,1'-dimethyl-4,4'-bipyridylium dicloride,
1,1'-di-2-hydroxyethyl-4,4'-bipyridylium dichloride,
1,1'-bis-3,5-dimethylmorpholinocarbonylmethyl-4,4'-bipyridylium dichloride
1-(2-hydroxyethyl)-1'-methyl-4,4'-bipyridylium dichloride,
1,1'-di-carbamoylmethyl-4,4'-bipyridylium dichloride,
1,1'-bis-N,N-dimethylcarbamoylmethyl-4,4'-bipyridylium dichloride,
1,1'-bis-N,N-diethylcarbamoylmethyl-4,4'-bipyridylium dichloride,
1,1-di-(piperidinocarbonylmethyl)-4,4'-bipyridylium dichloride,
1,1'-diacetonyl-4,4'-bipyridylium dichloride,
1,1'-diethoxycarbonylmethyl-4,4'-bipyridylium dibromide, or
1,1'-diallyl-4-4'-bipyridylium dibromide.

Of these 1,1'-ethylene-2,2'-bipyridylium dibromide and 1,1'-4-4'-dimethyl-bipyridylium dichloride are especially preferred.

The complexes of this invention are prepared by reacting the bipyridinium salts with the polysaccharide. In this invention, when very rapid hydration is desired, very low viscosity polysaccharide is preferred. When a slower hydration rate is desired, a higher viscosity polysaccharide may be used. The complexes are formed by mixing the bipyridinium salts and the polysaccharide and neutralizing the mixture. Several methods can be used; for example, pan agglomeration; drum drying, oven drying, or spray drying polysaccharide solutions; fluid bed dryer agglomeration; precipitation by a non-solvent of a bipyridinium/polysaccharide solution; and extrusion. Conveniently, neutralization is accomplished by introducing an alkali to the polysaccharide/bipyridinium salt mixture and then measuring and adjusting pH as necessary. Alternatively, a predetermined amount of alkali can be present in the polysaccharide or bipyridinium salt prior to mixing. Useful alkalis include ammonia, ammonium hydroxide, sodium hydroxide, and potassium hydroxide. These processes are described in greater detail below. Variations such as droplet size, drying temperature and time, concentration of ingredients, etc. are within the scope of this invention.

Pan Agglomeration

Powdered polysaccharide is placed in a pan agglomerator which produces a flowing bed of dry polysaccharide. A solution of bipyridinium salts is then sprayed onto the moving polysaccharide bed causing agglomeration of the polysaccharide powder into granules. The spray is produced through a nozzle which produces about a 500 micron droplet size. When all the polysaccharide has been agglomerated and all the bipyridinium salt solution is added, the agglomeration is then ammoniated with ammonia gas to a pH of 7.0 to 8.0, when measured on the damp granules. The complex granules are dried in a fluid bed dryer at an inlet temperature of 120° C. for 10 minutes. This produces a free flowing granular product containing a high concentration of active herbicide. A commercially available apparatus for this process is the Ferrotech Pan Agglomerator, model FC 016-02 (Ferrotech Co., Wyandotte, Mich.).

Drum Drying

The polysaccharide is mixed with the bipyridinium salt solution for ten minutes. This mixture is then ammoniated with either ammonia gas or 28% ammonium hydroxide solution. This produces a viscous, almost paste-like, liquid. After 15 minutes of additional mixing the complex is ready to be drum dried by conventional means.

Oven Drying/Spray Drying

When there is a greater amount of water in the system, instead of drum drying the complex can be dried in an oven or in conventional spray drying equipment.

Prilling

The polysaccharide is mixed with the bipyridinium salt solution for 10 minutes. This mixture is then ammoniated with either ammonia gas or 28% ammonium hydroxide solution. The complex is then heated slowly to 130° C. driving off 34% by weight of water. This hot condensed liquid complex is then dripped into a cold (5° C.) non-solvent fluid causing the complex to solidify into hard beads. The non-solvent is then removed through evaporation.

Extrusion

The polysaccharide is added to a bipyridium salt solution and mixed until the polysaccharide is dispersed. The mixture is then ammoniated under agitation with ammonia gas or ammonium hydroxide solution and then heated to 70° C. Mixing is continued for 30 minutes and then the hot mixture is transferred to an extruder where it is allowed to cool to ambient temperature. This forms the complex which may then be extruded to form either beads or strands of the complex.

Using these processes, complexes can be prepared with high concentrations of bipyridinium salts (14–55%, calculated as cation). Advantageously, when very low viscosity polysaccharide is used these complexes are easily soluble in water. Where rapid solubility is not necessary, higher viscosity polysaccharide can be used. The dissolved complexes can be used with commercial spraying equipment.

These complexes may also be formulated as solid herbicidal compositions of 5–55% concentration (calculated as cation) by the use of diluents which are very soluble in cold or hot water and which are essentially non-reactive with the bipyridinium salt. These diluents include the mono- and di-pentoses and hexoses such as glucose, fructose, arabinose, mannose, gulose, ribose, xylose, maltose, lactose, and sucrose and inorganic salts such as NaCl, KCl, $K_2HPO_4$, $K_2HSO_4$, $NH_4Cl$, $NH_4NO_3$, $(NH_4)_2SO_4$, $MgSO_4$, and $MgCl_2$. The diluents may be added before or after complex formation and before or after the complex is dried. Preferably, the diluents are added after complex formation and before drying.

The advantageous properties of the polysaccharide/bipyridinium complexes of this invention are not exhibited in other blends or complexes. Combinations with the following ingredients have been tested with paraquat.

| | Results |
|---|---|
| 1. Starch Graft Copolymers (U.S. Pat. No. 3,935,099) | Paraquat was absorbed but about |

| | Results |
|---|---|
| | 10% was permanently bound to the polymers, thus diminishing the herbicidal effect. |
| 2. Microcrystalline cellulose (Avicel 101) | Did not swell and imbibe the paraquat. |
| 3. Diatomaceous earth | Did not absorb paraquat. |
| 4. Cold water soluble tamarind gum (EP 11,951) | Paraquat was absorbed but crystallized on the particle surfaces. |
| 5. Polyacrylate solids (from Acrysol/RM-4) | Permitted crystal growth. |
| 6. Sodium lignosulfonate | Reacted with paraquat but formed insoluble precipitate. |
| 7. Carboxymethyl cellulose (Drispac Super Low) | Absorbed the paraquat but crystals formed on surface. |
| 8. Gum arabic | Permitted crystal growth and produced slow solubility rates. |

The complexes of this invention advantageously do not produce a floc when redissolved, for example, in hard water. As flocculation or particulate matter could potentially plug spray nozzles, the use of a clarified xanthan or guar is preferred. Clarification procedures such as enzyme treatment, filtration, etc. are well known for the production of heteropolysaccharides. Clarified products are also commercially available; for example, KELTROL ® T, a clarified xanthan gum.

The herbicidal use of the bipyridinium salts aer well known in the art. The solid complexes of the present invention, when dissolved, are usable as herbicides in the amounts, combinations, apparatuses, methods, etc. already well known to users of bipyridinium salts.

The invention is further defined by reference to the following preparations and examples, which are intended to be illustrative and not limiting. All viscosities were measured on a Brookfield LVT viscometer at 25° C.

EXAMPLE 1

Preparation from Xanthan Fermentation Broth

A. Low-viscosity xanthan gum

One hundred gallons (378.5 L) of xanthan gum fermentation broth coontaining approximately 4% xanthan gum having a viscosity of 6,000 cP, spindle 4, 60 rpm, was treated with proteolytic enzyme to partially clarify the solution. Based on weight of gum in the broth, 0.05% lysozyme was added to the broth and reacted for two hours. Then 0.5% HT Proteolytic 200 (Miles Labs) was added and reacted for four hours.

The fermentate was then heated to 140° F. (60° C.) and 0.05% ferrous sulfate plus 0.10% tetrasodium EDTA was added as a solution. 3.2 L of 11.67% hydrogen peroxide were then added in three portions over a period of two hours. The viscosity dropped to only 80 cP, spindle 2, 60 rpm, at which point the fermentate was cooled to 80° F. (26.6° C.) and neutralized to pH 7.5 using dilute potassium hydroxide. the xanthan gum was then precipitated with isopropanol, dried, and milled through 80 mesh.

B. Bipyridinium complex

A dry paraquat complex was prepared from the preceding xanthan gum using the following formulation:

89.0% Paraquat 3S solution (Chevron Chemical)
8.9% low viscosity xanthan gum
1.1% 28% ammonium hydroxide The xanthan gum was dissolved in the paraquat solution followed by the ammonium hydroxide. After mixing 30 minutes the liquid product was drum dried then milled and sized through 12 mesh on 30 mesh. The dry paraquat so produced was free flowing, contained 50% paraquat cation, and 0.50 g dissolved in 250 ml of 342 ppm hard water in less than one minute. In 250 ml water of 500 ppm hardness the solubility rate was only 70 seconds when used at a typical field use level of 0.1% paraquat cation. At aerial application rates of 1.0% paraquat cation the product dissolved in 250 ml of 500 ppm hard water in 90 seconds. No flocs were observed in any of these solutions.

EXAMPLE 2

Preparation from Dry Xanthan Gum 0.05% ferrous sulfate plus 0.10% $Na_4EDTA$ were dissolved in water followed by 5.0% enzyme clarified xanthan gum from Example 1(A) and 0.15% hydrogen peroxide. The solution was heated for 75 minutes at 75° C., at which time the viscosity dropped from 7500 cP, spindle 4, 60 rpm, to only 35 cP, spindle 1, 60 rpm. The solution was cooled, precipitated with isopropanol, dried, and milled through 80 mesh.

Production of the solid paraquat complex was performed as in Example 1(B). The complex dissolved in 250 ml of 342 ppm hard water in only 45 seconds at field use levels and in 250 ml of 500 ppm water in only two minutes at aerial use levels. No flocs were observed.

EXAMPLE 3

Preparation from Clarified Guar Gum 0.05% ferrous sulfate, 0.10% $Na_4EDTA$, and 0.20% hydrogen peroxide were dissolved in water in a water jacketed blender. Clarified guar gum (produced by cold filtration of a 0.3% solution through diatomaceous earth and precipitated with IPA) was slowly added as a dry powder to a final concentration of 10% gum. The temperature was maintained at 60° C. and the viscosity dropped from greater than 10,000 cP, spindle 4, 60 rpm, to 150 cP, spindle 2, 60 rpm, after only 15 minutes. After cooling the guar was precipitated with isopropanol, dried and milled through 40 mesh.

A dry paraquat complex from the degraded guar was then produced as in Example 1(B). The complex dissolved readily in 250 ml of 342 ppm hard water in two minutes ten seconds without floc formation.

EXAMPLE 4

Preparation from a Clarified Xanthan Gum/Clarified Guar Gum Blend

Thirty grams of a 1:1 blend of dry clarified xanthan gum and dry clarified guar from Examples 1 and 3 were added to 560 g hot water at 70° C. containing 0.4 g EDTA plus 0.1 g ferrous sulfate. Twenty-five grams of 3% hydrogen peroxide solution were then added in portions over a period of forty-five minutes. After 60 minutes the viscosity dropped from greater than 10,000 cP, spindle 4, 60 rpm, to only 85 cP, spindle 2, 60 rpm, at which point the gums were precipitated with isopropanol, dried, and milled through 80 mesh.

A dry paraquat complex was prepared from this blend as in Example 1(B). The dry paraquat dissolved in 250 ml of 342 ppm hard water in only 44 seconds at field use level and dissolved in 68 seconds at a level corresponding to aerial applications. The solutions contained no floc even after standing 24 hours. The blend performed as well as either gum separately. Since both products are effective, blends of the two gums in any ratio are possible.

EXAMPLE 5

Gum Viscosity vs. Solubility

The viscosity of the gum is important in determining the solubility rate of the paraquat complex. Table 5-1 shows this effect. Xanthan gum from fermentation broth was degraded as in Example 1 to various viscosity levels and the paraquat complex prepared. The solubility of the complex was then determined in 250 ml water containing 342 ppm hardness.

TABLE 5-1

| Sample | 5% Viscosity | Paraquat Complex Solubility Time |
|---|---|---|
| 1 | 35 cP | 43 sec. |
| 2 | 80 cP | 45 sec. |
| 3 | 140 cp | 68 sec. |
| 4 | 290 cP | 173 sec. |

EXAMPLE 6

Ultrafiltered Low Viscosity Xanthan Broth

A. Low viscosity gum

The viscosity of a 4% xanthan gum beer was broken using the metal catalyzed hydrogen peroxide reaction of Example 1(A). The gum from the broken beer was precipitated and dried. It was then reconstituted in water to 5% and showed a viscosity of 110 cP, spindle 2, 60 rpm.

The broken broth was then ultrafiltered under pressure using a membrane with a molecular weight cut-off of 18,000 and recirculated until a 30% solids solution was achieved. The viscosity of the concentrated broth was 2000 cP, spindle 4, 60 rpm, and a pH of 5.0.

B. Paraquat Complex Formulation in a 1:10 Ratio

A dry paraquat complex was prepared from the preceding xanthan gum using the following formulation:

75.2% Paraquat 3S Solution
23.9% Broth (concentrated)
0.9% 28% $NH_4OH$ Solution All three materials were mixed together and stirred for 5 minutes. The mixture was then drum dried at 235° F. (112.7° C.) surface temperature, milled and sized through 12 mesh on 30 mesh. The dry cmoplex showed no crystals.

0.50 g of complex dissolved in 250 ml of 342 ppm hardness water in 64 seconds. 5.0 g dissolved in 250 ml of 500 ppm hardness water in 71 seconds.

EXAMPLE 7

Herbicidal Application

Paraquat 3S (calculated at 1.7 mg cation) was sprayed onto 0.75 sq. ft. of St. Augustine grass. In like manner a xanthan/paraquat complex (calculated at 1.7 mg cation), as prepared in Example 1, was sprayed on an identical area of the same grass. After three days' exposure to sunlight, the grass in both areas was brown and dying, thus demonstrating the retained herbicidal activity of the complex.

EXAMPLE 8

Prilling

Production of the solid paraquat complex was performed as in Example 1(B) except the liquid complex was heated to 130° C., condensed and prilled in a non-solvent fluid (Cyclosol 52, Shell Chemical). The non-solvent was then evaporated in a fluid bed drier at 120° F. (48.9° C.) for 10 minutes. The bead size produced was through 4 mesh on 12 mesh screen. The complex dissolved in 250 ml of 342 PPM hard water in 90 seconds at field use levels. No free crystals were observed on the surface of the beads. No flocs were observed in the field use level solution.

EXAMPLE 9

Extrusion

| Formulation: | % (wt.) |
|---|---|
| Diquat HA (29.1% solution) | 87.9 |
| Low Visc. Xanthan | 11.0 |
| $NH_4OH$ (30% solution) | 1.1 |

Procedure:

With good agitation the xanthan gum was mixed into the diquat liquid till dispersed. Then aqueous ammonia was added and mixed well. This mixture was heated with agitation to 70° C. Mixing was continued for 30 minutes and then the hot mixture was transferred to an extruder and cooled down to ambient temperature to form a complex which was then extruded into mesh beads and 1" strands. The complex was extruded onto a non-stick surface and dried to 10–12% moisture level.

Test Data:

| | 10 MESH BEADS | 1" STRANDS |
|---|---|---|
| Solubility Rate | 65 sec. | 47 sec. |
| Appearance | no crystals | no crystals |
| Dusting | trace | trace |

EXAMPLE 10

Preparation from S-194

A hot 5% S-194 solution at 60° C. containing 0.05% $FeSO_4$ and 0.15% EDTA was prepared in a Waring blender, to which 3.0% hydrogen peroxide by weight of S-194 was added. The solution was held at 60° C. for 60 minutes by which time the viscosity dropped from greater than 10,000 cP, Brookfield LVT, sp. 4, 60 rpm to only 80 cP, spin. 1, 60 rpm. The solution was then cooled, precipitated in isopropanol, dried, and milled.

The production of the solid paraquat complex was performed as in Example 1(B). The S-194 complex dissolved in 342ppm hard water in 297 seconds and showed no free paraquat crystals.

EXAMPLE 11

Dry Flowable Arbotect®

The fungicide Arobtect® 20S (26.6% solids 2-(4-thiazoyl)benzimidazole hypophosphite solution) was converted to a 80% dry water soluble product using low viscosity xanthan gum.

®Registered Trademark, Merck & Co., Inc.

Formulation:

188.0 g Arbotect 20S 8.3 g Low visc. xanthan gum (90% solids)

Procedure:

The two materials were mixed for two hours. This mixture was then drum dried to 8.0% moisture, milled, and sized through 12 on 20 mesh.

Testing:

One gram of dry product was added to 100 ml water of 342 ppm hardness with mild agitation.

Solubility rate: 198 sec.;

Wetting: excellent;

Insolubles: none;

Appearance: very slightly turbid.

EXAMPLE 12

Xanthan Gum in Pesticides—Pan Agglomeration

Low viscosity xanthan gum was used as a binder system for dry flowable sulfur and thiabendazole formulations.

| Formulation I Sulfur | | Formulation II TBZ | |
| --- | --- | --- | --- |
| 90.0% | Sulfur Powder | 91.0% | TBZ Powder |
| 2.0% | Morwet EFW, surfactant, wetting agent. | 1.0% | Morwet EFW |
| 1.0% | Tamol SN, dispersant surface active ingredient | 1.0% | Tamol SN |
| 2.0% | Morwet D-425, dispersant, surface active ingredient | 2.0% | Morwet D-425 |
| 5.0% | Xanthan | 5.0% | Xanthan |
| 100.0% | Total | 100.0% | Total |

Procedure:

The dry materials were blended until uniform and the mixture then pan agglomerated using water spray to promote the rolling and sticking of the powder into beads. The beads were dried at 70° C., 30 minutes in a fluid bed drier. The dry granules were sized through 12 on 28 mesh.

Results:

|  | Formulation I | Formulation II |
| --- | --- | --- |
| Disintegration Rate | 93 Sec. | 100 Sec. |
| Wetting Rate | 65 Sec. | 8 Sec. |
| Dusting Rate | 4% | 5% |

EXAMPLE 13

Ammonium Chloride Diluent

| Formulation: | Wt. (g.) |
| --- | --- |
| Paraquat-CL2 Solution (362 G/L cation) | 319.4 |
| Low Visc. Xanthan | 30.0 |
| NH4OH (30% Solution) | 2.0 |
| NH4CL | 268.0 |

Procedure:

Under agitation, NH4OH was added to the Paraquat solution and mixed well. Then the gum was added and agitated 10 minutes. Using high shear, mixing continued for 10 more minutes. The sample was heated to 75° C. and then the NH4Cl was added slowly with good agitation. The mixture was reheated to 75° C. and held for 30 minutes, then drum dried at 120° C. surface temperature on the drum. The product was milled, sized and dried for testing.

This formulation yielded a 20% Paraquat cation dry system at 10% moisture.

Testing:

Appearance: Non-crystalline structure, tan in color, non-friable particles.

Solution Rate: In 300 ppm water a rate of 30 sec was achieved.

What is claimed is:

1. A solid, herbicidal bipyridinium quaternary salt-/heteropolysaccharide complex comprising 14–55% (wt.) bipyridinium salt, calculated as cation, wherein the heteropolysaccharide in said complex is a low viscosity heteropolysaccharide, wherein said heteropolysaccharide is xanthan gum or S-194 having a 5% (wt.) aqueous solution viscosity of 15–300 cP or guar gum having a 5% (wt.) aqueous solution viscosity of 15–100 cP as measured on a Brookfield LVT viscometer, at 25° C., spindle 2, 60 rpm.

2. A complex of claim 1 wherein the bipyridinium salt is 1,1'-ethylene-2,2'-bipyridylium dibromide, 1,1'-dimethyl-4,4'-bipyridylium dichloride, 1,1'-di-2-hydroxyethyl-4,4'-bipyridylium dichloride, 1,1'-bis-3,5-dimethylmorpholinocarbonylmethyl-4,4'-bipyridylium dichloride 1-(2-hydroxyethyl)-1' methyl-4,4'-bipyridylium dichloride, 1,1'-di-carbamoylmethyl-4,4'-bipyridylium dichloride, 1,1'-bis-N,N-dimethylcarbamoylmethyl-4,4'-bipyridylium dichloride, 1,1'-bis-N,N-diethylcarbamoylmethyl-4,4'-bipyridylium dichloride, 1,1-di-(piperidinocarbonylmethyl)-4,4'-bipyridylium dichloride, 1,1'-diacetonyl-4,4'-bipyridylium dichloride, 1,1'-diethoxycarbonylmethyl-4,4'-bipyridylium dibromide, or 1,1'-diallyl-4-4'-bipyridylium dibromide.

3. A complex of claim 1 wherein the heteropolysaccharide is xanthan gum and has a 5% solution viscosity of 200–300 cP.

4. A composition comprising a (1) diluent selected from the group consisting of mono- and di-pentoses and hexoses and inorganic salts and (2) a complex of claim 1 wherein said composition comprises 5–55% (wt.) bipyridinium salt.

* * * * *